United States Patent
Patterson, Jr. et al.

(10) Patent No.: US 9,737,625 B2
(45) Date of Patent: Aug. 22, 2017

(54) SANITIZING DEVICE

(71) Applicants: Sara Patterson, Jr., Tallahassee, FL (US); James Patterson, Tallahassee, FL (US)

(72) Inventors: Sara Patterson, Jr., Tallahassee, FL (US); James Patterson, Tallahassee, FL (US)

( * ) Notice: Subject to any disclaimer, the term of this patent is extended or adjusted under 35 U.S.C. 154(b) by 60 days.

(21) Appl. No.: 14/748,323

(22) Filed: Jun. 24, 2015

(65) Prior Publication Data

US 2015/0374867 A1    Dec. 31, 2015

Related U.S. Application Data

(60) Provisional application No. 62/017,464, filed on Jun. 26, 2014.

(51) Int. Cl.
| | |
|---|---|
| *A61L 2/20* | (2006.01) |
| *A61M 5/00* | (2006.01) |
| *A61L 2/14* | (2006.01) |
| *A61B 90/70* | (2016.01) |

(52) U.S. Cl.
CPC .............. *A61L 2/202* (2013.01); *A61B 90/70* (2016.02); *A61L 2/14* (2013.01); *A61M 5/001* (2013.01); *A61L 2202/24* (2013.01)

(58) Field of Classification Search
CPC ........ A61L 2/202; A61L 2/14; A61L 2202/24; A61L 2/10; A61L 2/24; A61L 9/12; A61L 2209/12; A61L 2202/121; A61L 2202/123; A61B 90/70; A61M 5/001; B01J 19/10; B01J 19/12; H01H 3/122; A47K 1/09; A61C 19/002
See application file for complete search history.

(56) References Cited

U.S. PATENT DOCUMENTS

| | | | |
|---|---|---|---|
| 4,806,770 A | 2/1989 | Hylton | |
| 4,888,487 A | 12/1989 | Ritter | |
| 5,029,252 A | 7/1991 | Ameseder | |
| 5,185,532 A * | 2/1993 | Zabsky | A61L 2/10 250/455.11 |
| 6,461,568 B1 | 10/2002 | Eckhardt | |
| 8,941,078 B2 * | 1/2015 | Tantillo | A63H 33/006 250/453.11 |
| 2010/0061887 A1 * | 3/2010 | Harper | A61L 2/10 422/24 |
| 2010/0143188 A1 * | 6/2010 | Roiniotis | A61L 2/10 422/24 |

* cited by examiner

*Primary Examiner* — Xiuyu Tai
(74) *Attorney, Agent, or Firm* — J. Wiley Horton

(57) ABSTRACT

A sanitizing device used to sanitize a bulb syringe. The device preferably includes a base, a bulb receiver, and a sanitization system. The sanitization system produces a sanitizing gas that is propelled into and possibly around a bulb syringe in order to sanitize the surfaces of the syringe. The sanitization system preferably includes an ionization module, a fan, electrodes, and a power supply. Preferably, the sanitization system is housed in a conical housing which includes a central nozzle and an array of openings centered around the nozzle exit. The sanitization device preferably includes an automatic switch that is activated by the presence of a bulb syringe or upon placing a cover over the device.

20 Claims, 14 Drawing Sheets

SANITIZING DEVICE

CROSS-REFERENCES TO RELATED APPLICATIONS

This non-provisional patent application claims the benefit of an earlier filed provisional patent application. The provisional application was assigned Ser. No. 62/017,464. It was filed on Jun. 26, 2014.

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of sanitizing devices. More specifically, the invention comprises a device which sanitizes the inner and outer surfaces of a bulb syringe.

2. Description of the Related Art

A prior art bulb syringe is shown in FIG. 1. Bulb syringe 10 includes a spherical end 12 and an open end 14. Spherical end 12 creates the "bulb" of the syringe, while a long, narrow conduit forms down to open end 14—creating a syringe-type shape, as illustrated. Open end includes a centrally located hole, and the entire device is hollow. Typically, a bulb syringe is fabricated from a soft plastic material. This allows the user to create suction by squeezing the bulb. Using this suction, the user can draw liquid into the bulb. Then, the user can squeeze the bulb in order to force the liquid from the hole located at open end 14. This is useful for many applications, as discussed in the following text.

There are many uses for a bulb syringe. For example a bulb syringe can be used to draw earwax from a user's ear. In addition, a bulb syringe can be used as an enema. While these uses are valuable, the primary use of a bulb syringe known in the art is to draw mucus from a baby's nose and mouth.

The current invention focuses primarily on using a bulb syringe to draw mucus from the mouth and nose of a baby. When a baby is sick, a mother or father is required to extract the mucus from the mouth or nose of the baby in order to alleviate congestion. Unfortunately, young children are incapable of ridding themselves of the mucus in the ways that adults or older children cars expel mucus. Thus, the suction created by the bulb syringe allows the user to manually remove the mucus. While it depends on the severity of the illness, drawing mucus from the nose and/or mouth of the baby should be done frequently. Typically alter each use, the user cleans out the bulb syringe using a bowl of warm, soapy water. By drawing the water in and expelling it, the user may remove the mucus from the bulb of the syringe. However, this does not sanitize or disinfect the syringe.

There are methods, other than using a bulb syringe which allow a user to extract mucus from the nostrils of a baby. One such technique is to use a cotton swab to clean out the nostrils. However, this technique is not as effective as using a bulb syringe. Another method used to remove the mucus from a baby's nose is to siphon the mucus out using a tube and the mouth of the adult/caretaker. Much like siphoning gas or water, the caregiver inserts a tube into the baby's nose and creates suction with his or her mouth. The disadvantages of this technique stem mainly from the chance of sucking mucus into the user's mouth and disinfecting and cleaning the tube.

Thus, it is evident that a bulb syringe is the most effective tool that can be used in order to remove mucus from the nose of a baby. However, there are sanitation issues that stem from trapping viruses, bacteria, and moisture in the bulb that just are not addressed with soapy, warm water. Therefore, what is needed is a device which allows a user to quickly and effectively disinfect a bulb syringe.

There are several known technologies in the art which are currently used to sanitize/purify air, surfaces, and water. One such method is the use of ultraviolet light. Ultraviolet C or "UVC" light includes light having a wavelength between 100 nm and 280 nm. More particularly, when microorganisms, such as viruses, bacteria, etc., are exposed to 240-280 nm UV light the organisms are destroyed. The UV radiation destroys the nucleic acids in the organisms, which disrupts their DMA and leaves them unable to perform vital cell functions. However, in order to be successful, the surface, air, or medium to be sanitized must be exposed directly to the ultraviolet light. In addition to direct "line-of-sight" sanitization, UV light can also be used to create ozone. Since ozone readily gives up an oxygen atom, free ozone molecules act as powerful oxidizing agents, thereby destroying microorganisms which interact with the ozone.

Another method of sanitization commonly used is ionization of air. An air ionizer uses electrostatically charged electrodes to charge particles in the air. These particles then interact with organisms and particles in the air or on surfaces. Then, the charged particles form and/or break bonds with the harmful molecules in the air, breaking them down into harmless molecules and compounds. Typically, ionizers use negative ions to achieve this. However, some ionizers create both anions and cations, which increases the effectiveness of the ionizer. This technique is commonly referred to as bi-polar ionization. Using bi-polar ionization allows the charged particles to react with both negative and positive (or negatively and positively susceptible) particles as opposed to just one or the other.

The present invention achieves the objective of sanitization of a bulb syringe using one or more sanitization methods. This objective, as well as others, are explained in the following description.

BRIEF SUMMARY OF THE INVENTION

The present invention comprises a sanitizing device used to sanitize the inner surfaces, outer surfaces, and surrounding air of a bulb syringe. The device preferably includes a base, a bulb receiver, and a sanitization system. Preferably, the sanitization system uses bi-polar ionization to create positive and negative ions. These ions are dispersed into and around a bulb syringe in order to sanitize the surfaces of the syringe. The sanitization system preferably includes an ionization module, a fan, electrodes, and a power supply. Preferably, the sanitization system includes a central nozzle and an array of openings centered around the nozzle exit.

The sanitization device preferably includes an automatic switch that is activated by the presence of a bulb syringe or upon placing a cover over the device. This allows the user to activate the device by simply inserting a bulb syringe into the receiving end of the device which includes a central opening which is intended to receive a bulb syringe.

Figure 1:
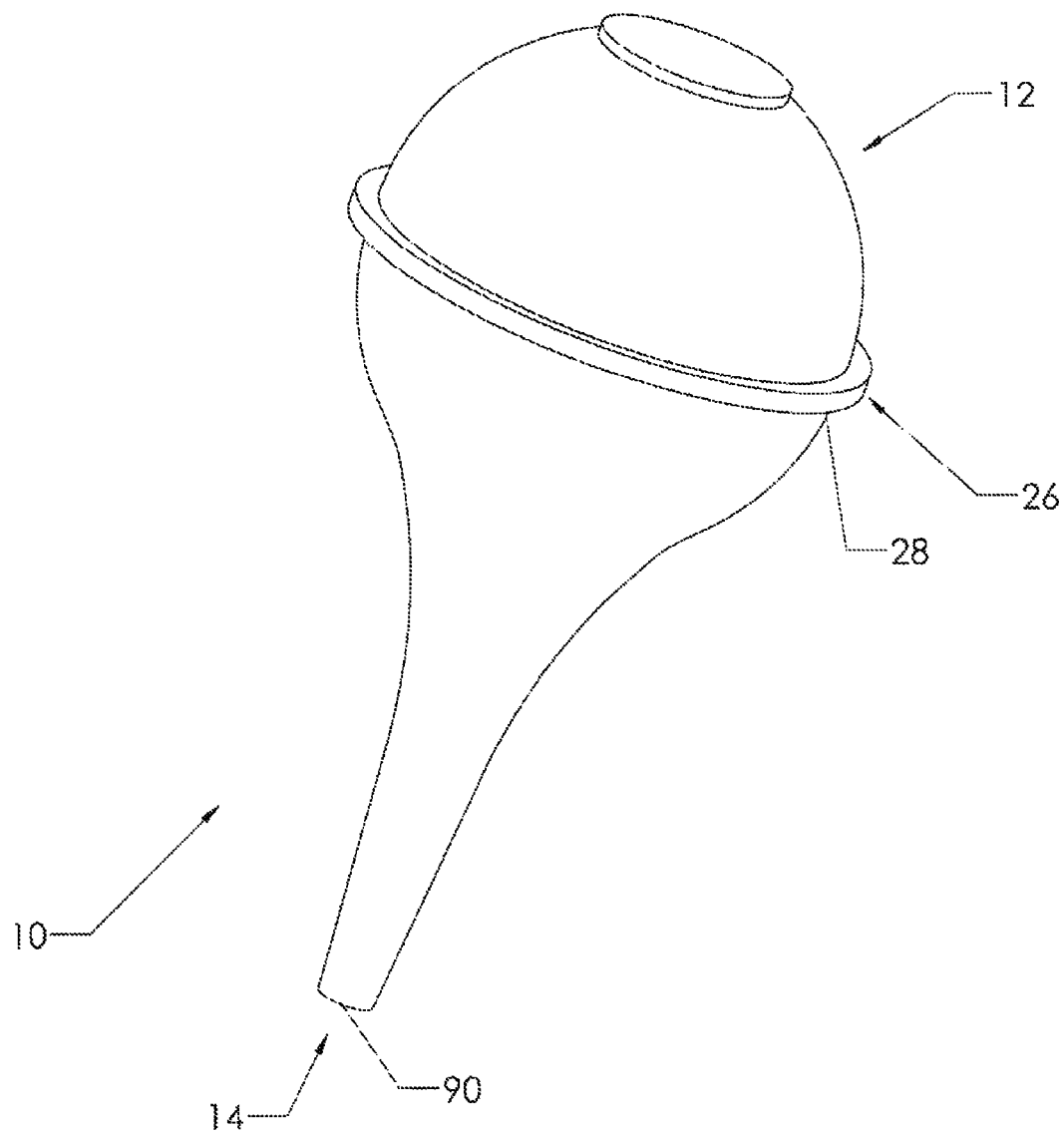
FIG. 1 is a perspective view, showing a prior art bulb syringe.

REFERENCE NUMERALS IN THE DRAWINGS 10 bulb syringe
12 spherical end
14 open end
16 sanitizing device
18 receiving end
20 collection pad
22 receiving end opening
24 drainage slot
26 rib
28 downward facing surface
30 upward facing surface
48 transmitter
50 light beam
52 bulb receiver
54 line of sight
56 light receiver
60 main body
62 sanitizing device cover
64 base
66 sanitization system housing
68 sanitization system
70 support
72 sanitization system cover
74 ionization module
76 fan
78 power supply
80 electrode
82 ultraviolet light bulb
84 nozzle
86 nozzle exit
88 nozzle exit centerline
90 opening
92 opening array
94 switch
96 status panel
98 light emitting diode
100 retaining device
102 attachment hook
104 basket
106 pacifier

DETAILED DESCRIPTION OF THE INVENTION

Figure 2:
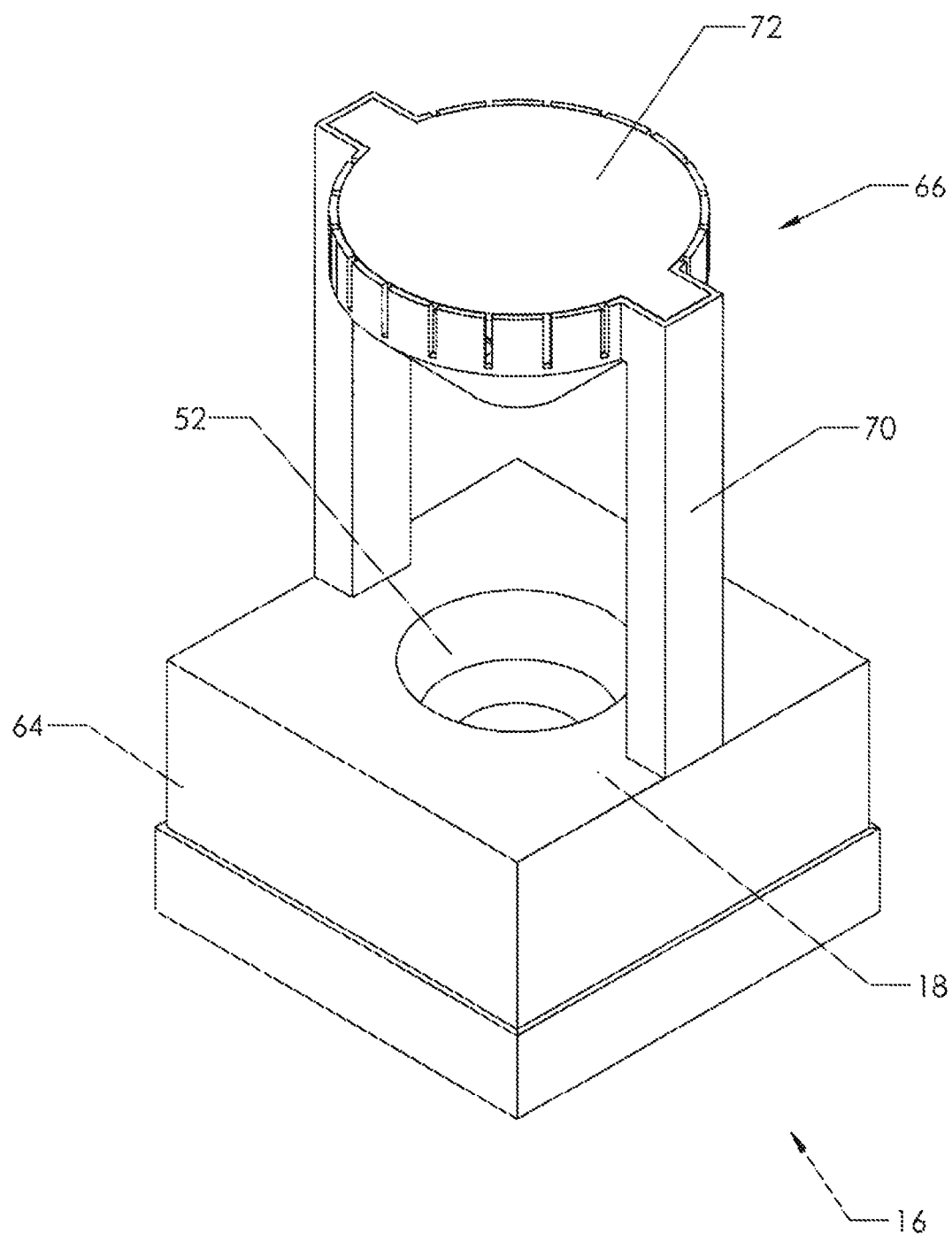
FIG. 2 is a perspective view, showing an embodiment of the present invention.

The present invention provides a device for sanitizing a bulb syringe (such as bulb syringe 10 shown in FIG. 1) and other objects. FIG. 2 shows an embodiment of the present invention. Sanitizing device 16 preferably includes base 64, receiving end 18, bulb receiver 52, and sanitization system housing 66. In this embodiment, bulb receiver 52 is located within base 64 and sanitization system housing 66 is connected to base 64 via supports 70. Preferably, sanitization system housing 66 contains the sanitization system. In the current view, the internal components of the sanitization system are hidden by sanitization system cover 72. Preferably, sanitizing device 16 is small enough to easily sit on a typical household table or countertop. Those familiar with the art will realize that a device designed to sanitize a bulb syringe 10 and other similarly sized objects can easily sit on a counter or table. In addition, sanitizing device 16 may be battery powered or include a power cord to be plugged into the wall. Furthermore, sanitizing device 16 may include a rechargeable battery whereby the user can recharge the device using a power outlet. Battery power would allow the user to sanitize objects while traveling (or otherwise away from a power source) if electricity outlets are unavailable.

Figure 3:
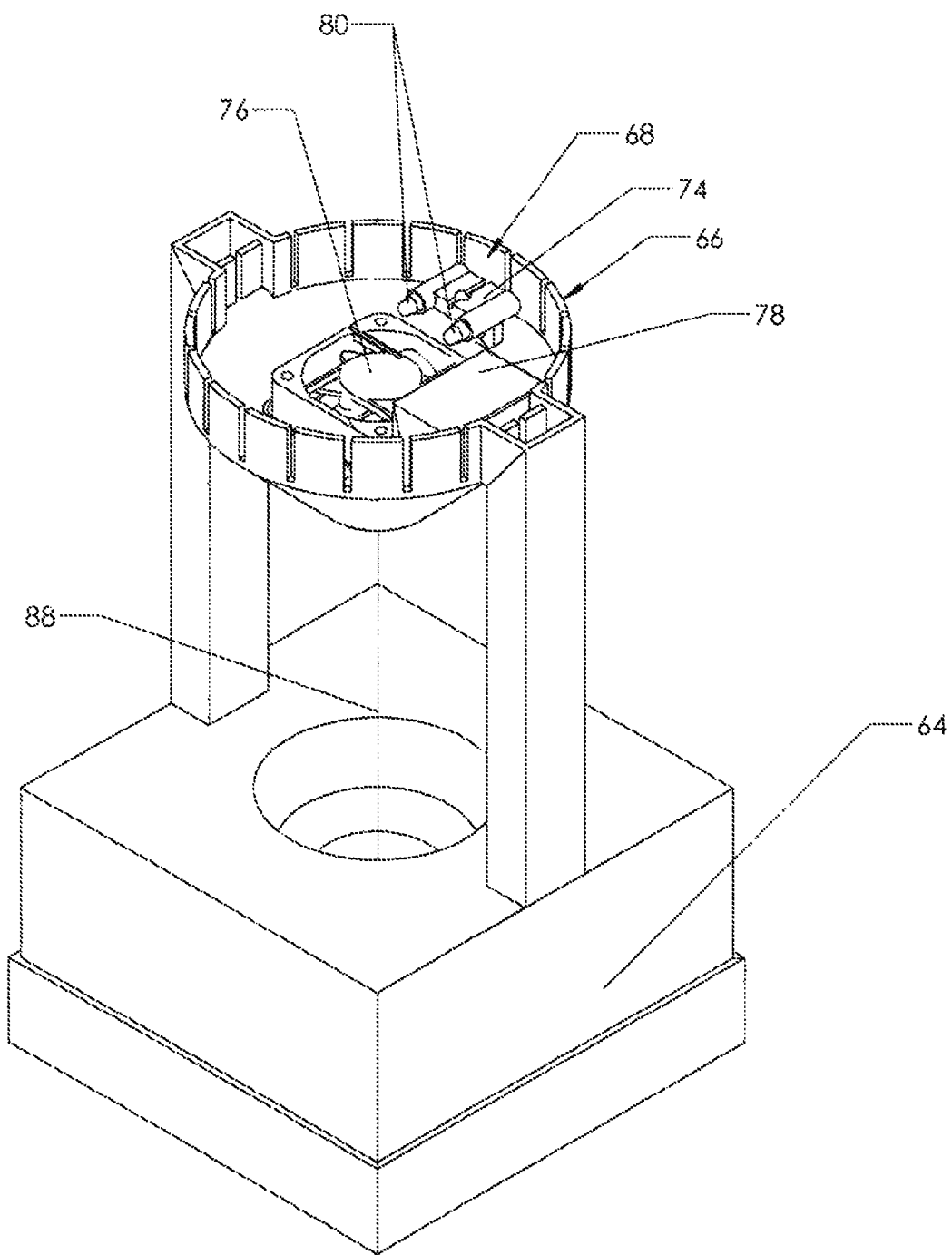
FIG. 3 is a perspective view, showing the embodiment of FIG. 2 with the sanitization system housing cover removed.

FIG. 3 shows sanitization system housing 66 with sanitization system cover 72 removed, thereby exposing sanitization system 68. Preferably, sanitization system 68 includes ionization module 74, fan 76, and power supply 78. Ionization module 74 is powered by power supply 78. Although power supply 78 is shown within sanitization system housing 66, it may be too large in some instances to fit within housing 66. Ionization typically requires a high voltage in order to create the electrical discharge necessary to ionize particles in the air—in which case power supply 78 can be included within base 64.

Preferably, ionization module 74 includes electrodes 80. Preferably, electrodes 80 create an electrical discharge. This discharge ionizes molecules in the air (This includes water vapor in the air) creating ions. Since ionization module 68 is a bi-polar module, both negative and positive ions are created. These ions bond with bacteria, viruses and other undesirable compounds, thereby breaking the original bonds. This, in the case of microorganisms, destroys the organisms. In the case of other undesirable compounds, such as volatile organic compounds ("VOCs"), the ions bond and/or trade electrons breaking down the VOCs to harmless compounds. The technique used to disperse these ions is discussed further in the following text.

Those familiar with art will realize that negative, positive, and bi-polar ionization are effective at destroying particles in the air and on surfaces. Ionization allows a user to ionize particles in the air and disperse those particles to surfaces and the air in order to destroy microorganisms and other VOCs. Therefore, ionization is widely used in air purifiers as well as instrument sanitization. Thus, bi-polar ionization is an effective method of sanitization to be used in the present invention.

Figure 4:
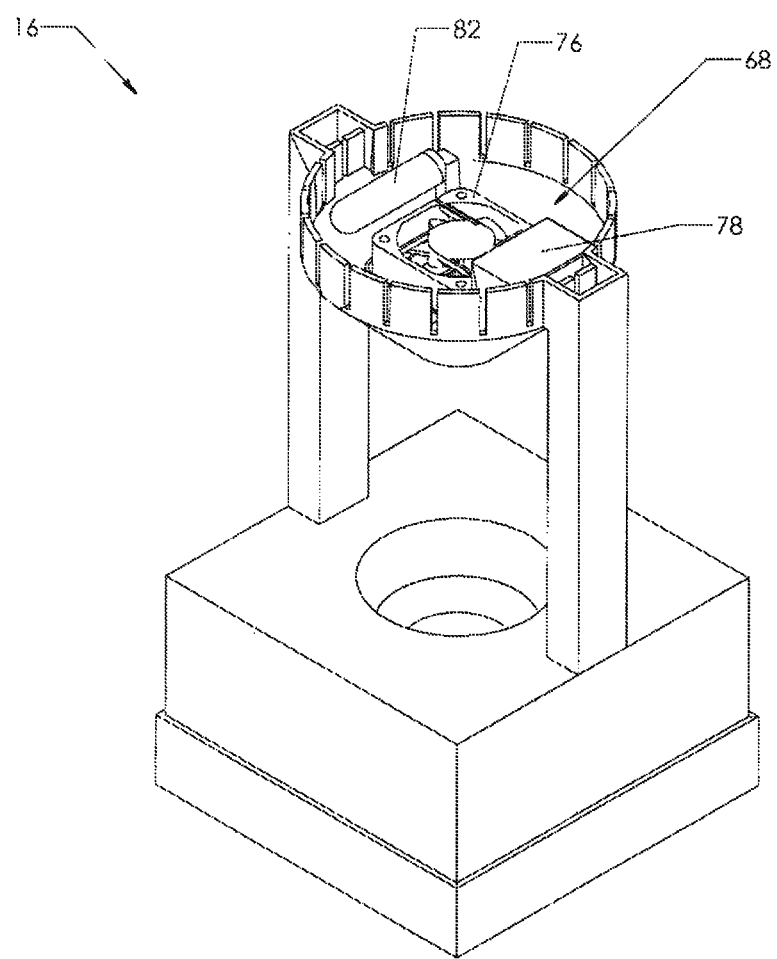
FIG. 4 is a perspective view, showing an alternate embodiment of the present invention with the sanitization system housing cover removed.

FIG. 4 shows another embodiment of sanitizing device 16 which uses an ozone based sanitization system 68 to sanitize objects. In this embodiment, sanitization system 68 preferably includes fan 76, power supply 78, and ultraviolet ("UV") light bulb 82. Preferably, UV bulb 82 radiates light at a wavelength which creates ozone. Those familiar with the art will realize that a UVC light bulb produces light at wavelengths of 254 nm and 185 nm. In addition, for production of ozone, 185 nm is preferably the dominant wavelength. While similar to ionization, ozone production is accomplished using UV light to attract extra oxygen in order to form ozone molecules, which then interact with undesirable compounds and molecules in the air or on surfaces.

Figure 5:
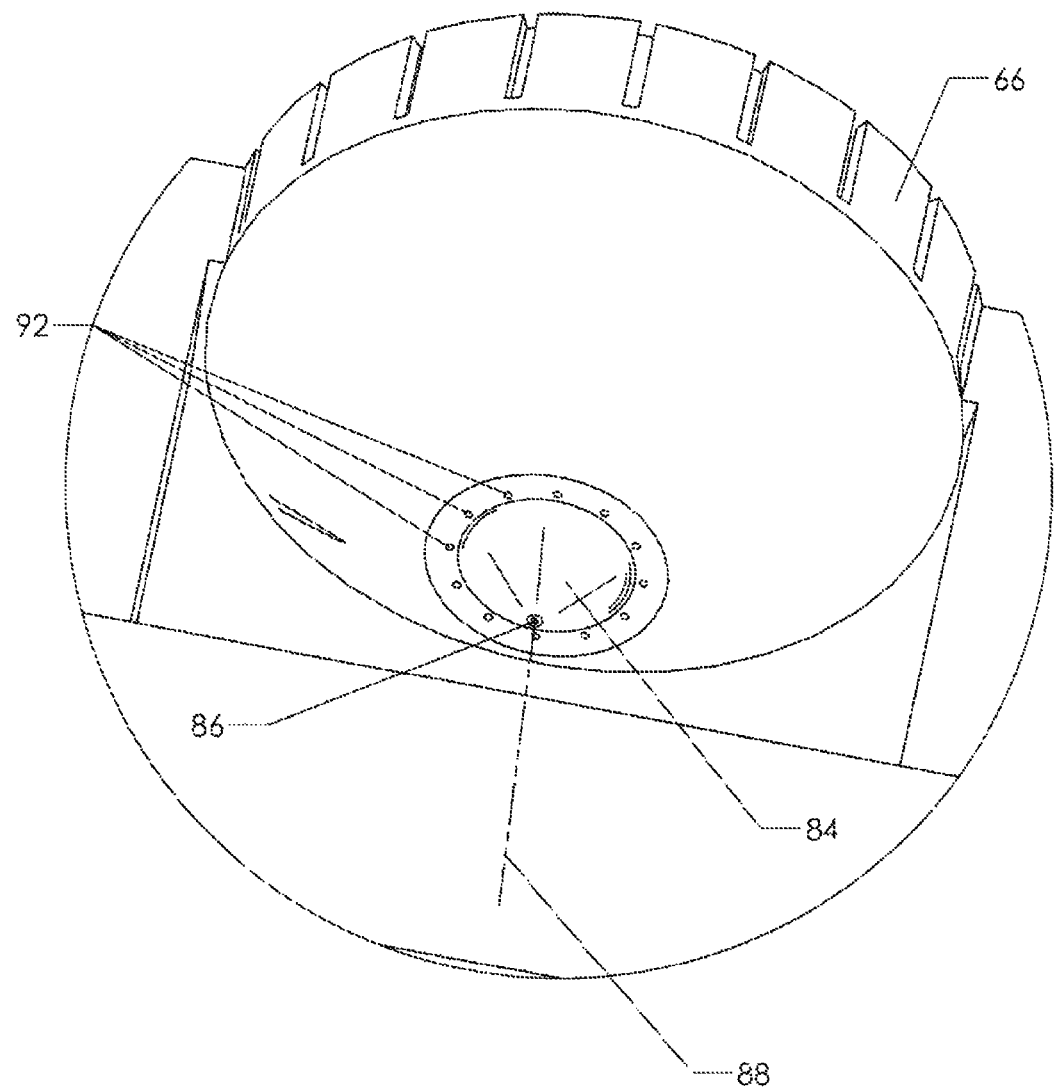
FIG. 5 is a detailed view, showing a preferred nozzle arrangement used in the present invention.

FIG. 5 shows a detailed view of the underside of sanitization system housing 66. Now referring to FIGS. 3 and 5, the method of sanitizing a bulb syringe 10 is explained. As illustrated, the side of sanitization system housing 66 facing the base is preferably conical. Nozzle 84 (also preferably a conical shape) protrudes in the same direction. Nozzle exit 86 is located at the tip of nozzle 84. In order to properly orient the reader between the two figures, nozzle exit centerline 88 is shown in FIGS. 3 and 5.

Staying with FIG. 3, once ionization module 74 has been activated, electrodes 80 begin to discharge. This creates positive and negative ions in the top portion of housing 66. At the time of activation of module 74, fan 76 is also given power and activated. As illustrated, fan 76 is axially aligned with nozzle exit 86 and configured to force air toward nozzle exit 86. Thus, as electrodes 80 create ions, fan 76 forces the ions downward toward nozzle 84. These ions then flow through nozzle exit 86. Those familiar with the art will note that the conical shape of system housing 66 acts to funnel ions or ozone down into nozzle 84.

Figure 6:
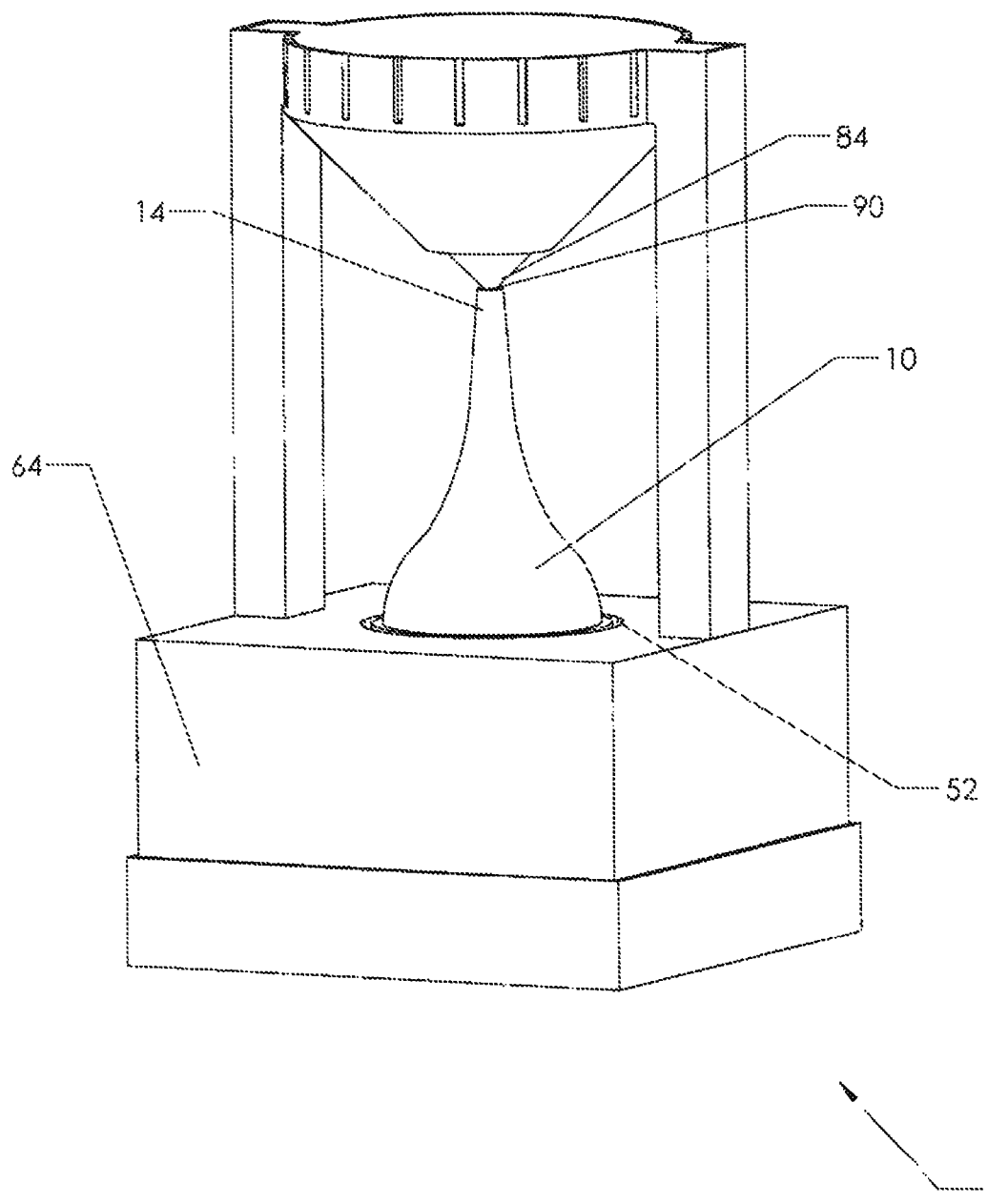
FIG. 6 is a perspective view, showing the present invention with a bulb syringe resting in the bulb receiver.

FIG. 6 shows bulb syringe 10 placed into sanitizing device 16. Preferably, spherical end 12 rests within bulb receiver 52. The reader will note that bulb syringe 10 is positioned such that nozzle 84 is inserted into the opening 90 of syringe 10, which causes open end 14 of nasal bulb 10 to be axially aligned with nozzle 84 and nozzle exit 86. This orientation allows positive and negative ions to be forced through nozzle exit 86 via fan 76, and into opening 90 of bulb syringe 10. Those familiar with the art will note that, preferably, the user has cleaned the inside and outside of bulb syringe 10 with warm, soapy water. Although this does not kill bacteria, viruses, or other VOCs located within the syringe 10, it does clean out mucus and other fluids which may have accumulated during use of the syringe 10. Preferably, by feeding ions into syringe 10 using fan 76, there are more ions inside which allow for more reactions, thereby destroying more microorganisms/VOCs. Those familiar with the art will realize that without fan 76 ions would still flow into syringe 10, but with less energy and in lower numbers. Of course, the more ions available to react with VOCs, the more reactions which will occur.

As ions enter bulb syringe 10, reactions occur between those ions and particles within bulb syringe 10. Ions react with microorganisms and other harmful compounds/molecules on the inner surface of bulb syringe 10 and in the air within syringe 10. By destroying bacteria and viruses and reacting with other harmful molecules to create harmless molecules, the ions successfully sanitize bulb syringe 10.

Referring back to FIG. 5, the reader will note that the underside of sanitization system housing 66 preferably includes opening array 92 (an array of additional openings that are smaller than 86). Preferably, opening array 92 includes at least two openings arranged around the perimeter of nozzle 84, as illustrated. Opening array 92 allows ions to interact with compounds on the outer surface of bulb syringe 10, thereby sanitizing the outer surface of bulb syringe 10 as well as the inside. While there is likely more concern for bacteria, viruses, and VOCs inside bulb syringe 10, it is also important to sanitize the outer surfaces of syringe 10.

Those familiar with the art will realize that the orientation of bulb syringe 10 in FIG. 6 is such that opening 90 is facing upward. Thus, any liquid or particles will remain within bulb syringe 10 during sanitization. In this embodiment, leakage of water or other fluids or particles is not an issue.

The reader will note that although the foregoing was explained using bi-polar ionization as the sanitization technology, this description also applies to the embodiment shown in FIG. 4. As UV light bulb 82 creates ozone, fan 76 forces ozone particles into and around bulb syringe 10. Similar to ions, ozone reacts with harmful molecules on the surface and in the air, thereby sanitizing the device. The reader will also note that ionization is the preferred embodiment of the present invention for sanitization system 68.

Figure 7:
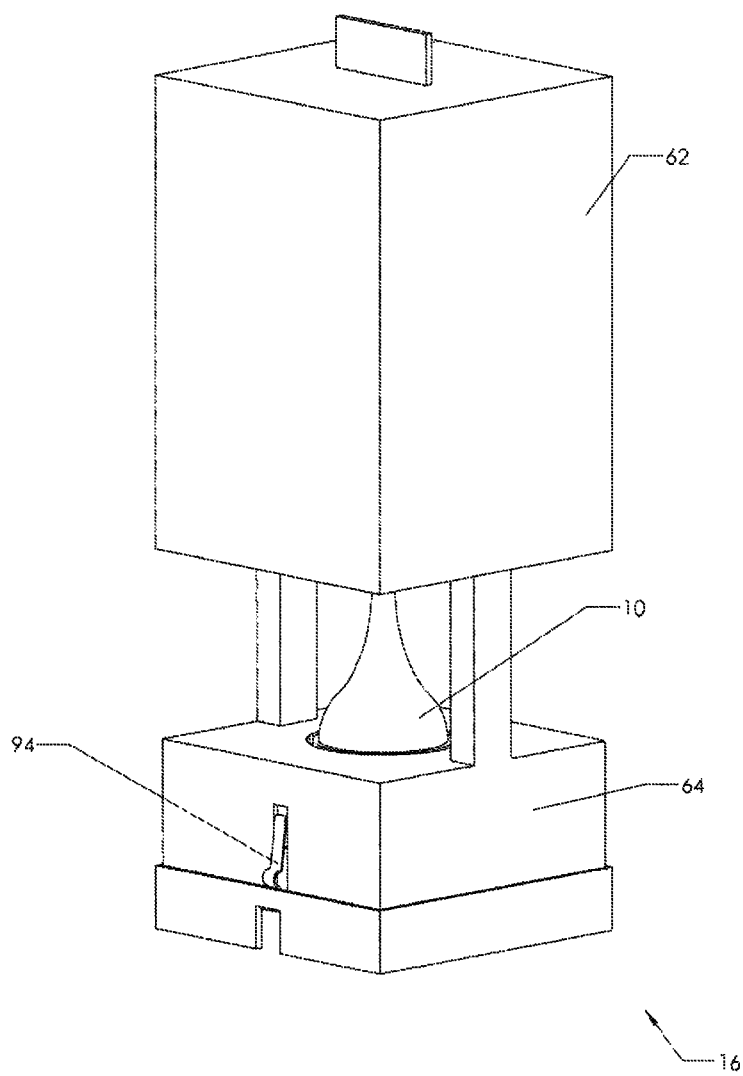
FIG. 7 is a perspective view, showing an exemplary activation switch.
Figure 8:
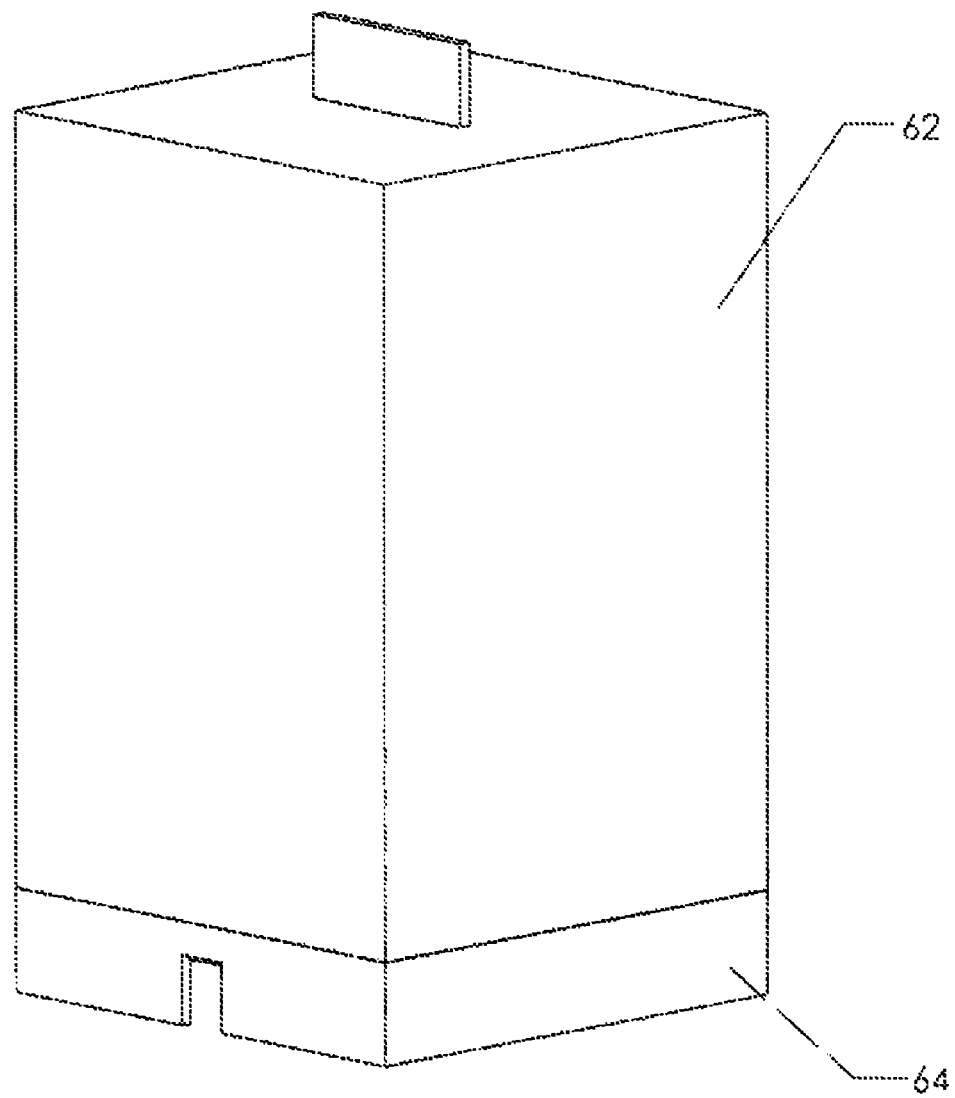
FIG. 8 is a perspective view, showing the embodiment of FIG. 7 with a device cover resting on the base of the sanitizing device.

Preferably, sanitizing device 16 includes sanitizing device cover 62. This is illustrated in FIGS. 7 and 8. FIG. 7 shows device cover 62 as it is being placed onto device 16. FIG. 8 shows device cover 62 fully on and resting on base 64. In this embodiment of the present invention, device cover 62 serves three main purposes. First, device cover 62 allows sanitizing device 16 and bulb syringe 10 to remain undisturbed while device 16 is sanitizing syringe 10. Second, once cover 62 is in the closed position (FIG. 8), sanitizing device 16 is activated. Preferably, base 64 includes switch 94. Preferably, switch 94 is a "normally open" type switch. Thus, in order to activate sanitization system 68, the switch 94 must be pressed, or "closed." As illustrated, this occurs when cover 62 is placed over base 64. As the user places sanitizing device cover 62 over base 64, the sanitizing process begins. Third, sanitizing device cover 62 allows the ions (or ozone) produced by sanitization system 68 to accumulate within the chamber created. As those familiar with art will realize, a concentration of ions within the chamber allow for more reactions with undesirable compounds. Finally, cover 62 prevents ions or ozone from spreading throughout the surrounding environment during sanitization.

In a preferred embodiment of the present invention, the method of activation of sanitization system 68, such as switch 94, is on an automatic timer. The timer is activated once switch 94 is closed. Preferably, the timer resets upon opening of switch 94. This accounts for a user accidentally pressing switch 94 or taking cover 62 off of base 64 before the device has had time to run a full cycle. Including a timer with switch 94 allows the free ions/ozone to dissipate within the closed chamber prior to removing cover 62. Otherwise, sanitization system 68 would continue generating ozone/ions until the user removed cover 62. While this may not be an issue, if the user accidentally left cover 62 in place for much longer than the recommended sanitization time an accumulation of ozone could be hazardous.

Figure 9:
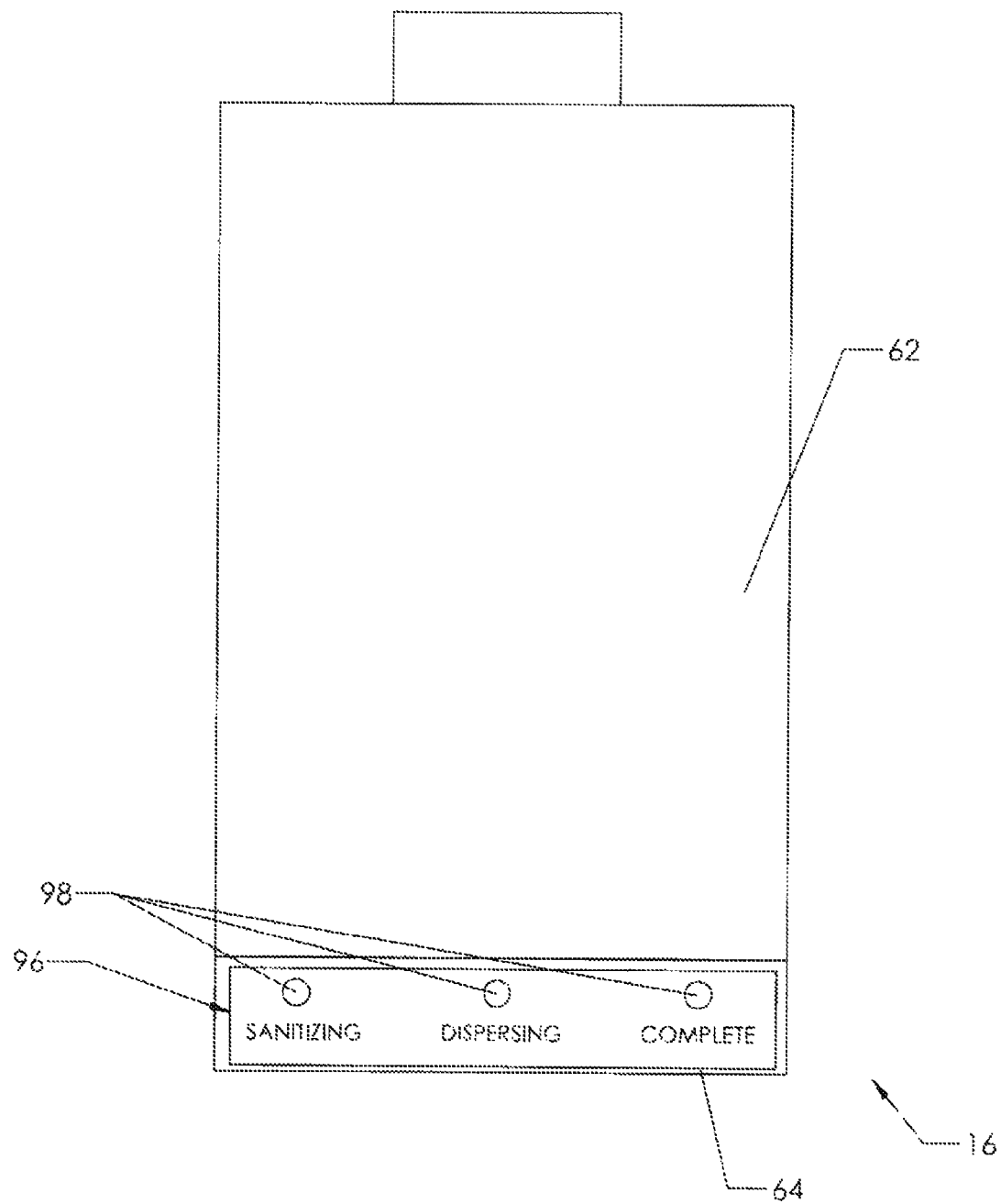
FIG. 9 is an elevation view, showing the inclusion of a status panel with indicator lights.

FIG. 9 shows a front view of sanitizing device 16 with cover 62 in place. In a preferred embodiment of sanitizing device, a status panel 96 is included on base 64. Status panel 96 indicates the stains of sanitization cycle. In the simplest embodiment, stains panel 96 is a series of colored light emitting diodes ("LEDs"). In a preferred embodiment (as illustrated in FIG. 9), there is text next to a series of LEDs wherein each LED is illuminated based on the status and progression of the sanitation timeframe. Once cover 62 is placed on base 64, sanitization system 68 is activated, along with a timer and the LED adjacent to the word "SANITIZING." Once the sanitizing period is done, the timer deactivates sanitization system 68. At this point the LED adjacent to the word "SANITIZING" may remain illuminated or another LED adjacent another word or phrase, such as "DISPERSING." Once the sanitization is complete, an LED adjacent to the phrase "CYCLE COMPLETE" is illuminated. Of course, this could be done using a digital screen which simply displays the text discussed. Those familiar with the art will appreciate that there are many ways to indicate the states of the sanitization cycle. In addition, sanitizing device 16 may include a locking mechanism which does not allow the user to remove device cover 62 until the cycle is complete.

Figure 10:
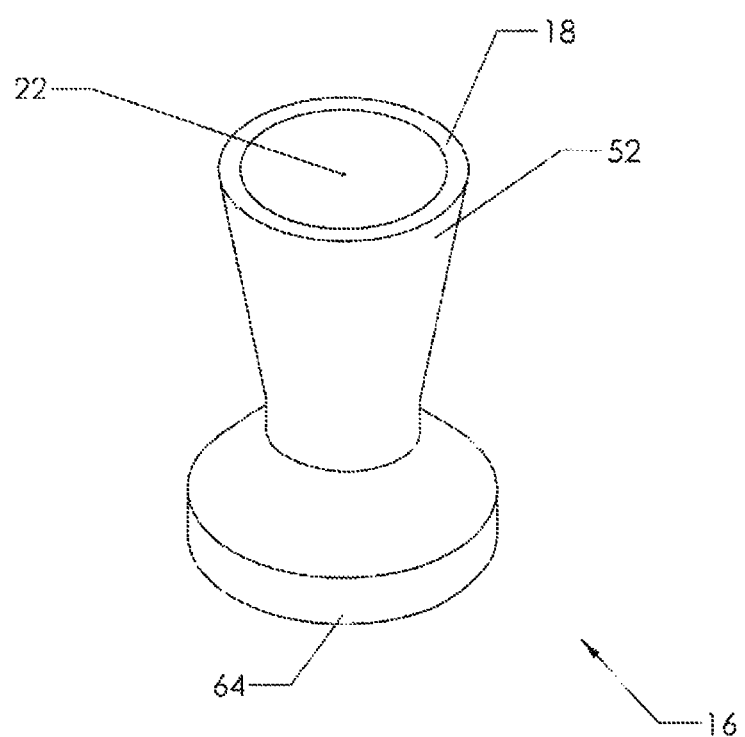
FIG. 10 is a perspective view, showing another embodiment of the present invention in which the bulb orientation is inverted.

FIG. 10 shows another embodiment of sanitizing device 16. Contrary to the orientation of the previous embodiment, the base 64 of current embodiment includes sanitization system housing 66 and sanitization system 68. In addition, receiving end 18 and bulb receiver 52 are not located within base 64, but on the opposite end of base 64, as illustrated. This allows the user to load bulb syringe 10 from the top by simply placing bulb syringe 10 on bulb receiver 52. Sanitizing device 16 preferably includes receiving end opening 22 proximate receiving end 18.

Figure 11:
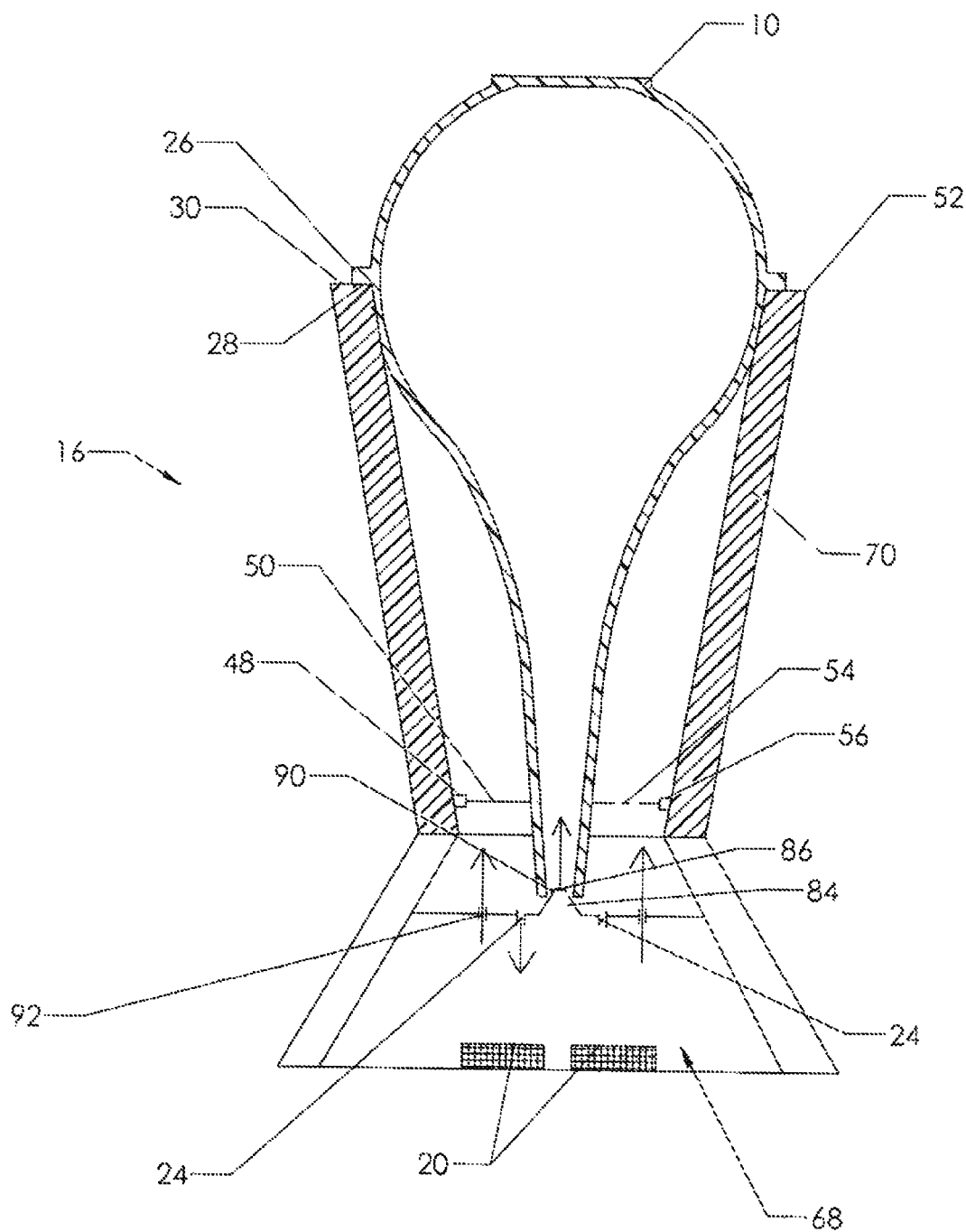
FIG. 11 is a sectional elevation views showing the embodiment of FIG. 10 with a bulb in place.

FIG. 11 shows this embodiment of the sanitizing device 16 with bulb syringe 10 resting on bulb receiver 52. The reader will note that the view is a partial section view. In this embodiment, sanitization housing 66 is incorporated within base 64. As with the previous embodiment, support 70 connects sanitization housing 66 to receiver 52. Components of sanitization system 68 have been shown in simplified form in the view. As illustrated, receiving end 18 receives bulb syringe 10. A typical prior art bulb syringe 10 includes rib 26 which extends over the upward facing surface of receiving end 18. As illustrated in FIG. 11, the downward facing surface 28 of rib 26 rests upon the upward facing surface 30 of sanitizing device 16. Thus, the bulb syringe may be lowered into position but it cannot pass completely through the sanitizing device 16. Although this particular illustration shows bulb syringe 10 having rib 26, the reader will note that if rib 26 is absent, bulb syringe will still rest at a desired height (and will not be allowed to pass through sanitizing device 16) by simply adjusting the inner radius of receiving end 18. Rib 26 has been included because the most widely used bulb syringe 10 includes a rib 26. Fortunately, the lower surface 28 of rib 26 provides a flat surface for bulb syringe to rest upon, thereby creating a more stable connection. In addition, because both surfaces are flat, proper alignment of the bulb syringe within the sanitizing device is less difficult to achieve.

In a preferred embodiment of the present invention, sanitizing device 16 is activated using a photoelectric sensor. FIG. 11 demonstrates an opposed-beam, or through-beam photoelectric sensor system. The opposed system includes a transmitter 48, a light beam 50, and a light receiver 56. An opposed system is arranged such that the light receiver 56 is within the line of sight 54 of the transmitter 48, as shown. An object is detected when light beam 50 is not detected by receiver 56. This system allows the user to simply place bulb syringe 10 into disinfectant device 16 after bulb syringe 10 has been rinsed with warm, soapy water. Upon breaking beam 50, the sanitization sequence is preferably triggered by light receiver 56. Then, when the bulb syringe is removed, the beam is unbroken and the system is shut down. Thus, the user is not required to turn the device on or off. In addition, the photoelectric switch acts as a safety mechanism by only activating sanitation system 68 when the beam is blocked. Although a preferred embodiment using a photoelectric sensor is shown, sanitizing device 16 may be activated just as easily using a manual switch with or without a timing unit. Preferably, there is a timing unit incorporated with the invention which shuts down the device after a predetermined amount of time (preferably, the time it would take to sanitize the bulb syringe). In addition, it is preferred that the unit includes an indicator that informs the user that the bulb syringe has been sanitized (shown in FIG. 9).

The arrows shown in FIG. 11 depict the movement of air after the system has been activated. The details of creating ions/ozone has been discussed at length in the preceding text so that discussion and those components are not included here. Due to the reverse orientation of the present embodiment, nozzle 84 (coupled with fan 76) three ions upward into bulb syringe 10. This is indicated by the arrow exiting nozzle exit 86. In addition, arrows indicate ions traveling upwards from opening array 92. Also due to the reverse orientation of this embodiment, sanitizing device 16 includes drainage slot 24 and collection pads 20. Because opening 90 is facing downward, any remaining liquid will drip out of bulb syringe 10 during sanitization via opening 90. On the contrary, in the previous embodiment shown in FIGS. 2-3, any remaining liquid will remain in the spherical end 12 of the syringe 10 during sanitization. While in this embodiment, that liquid can flow down the sides of nozzle 84 and into drainage slot 24. Collection pads 20 preferably collect any liquid dripping form drainage slot 24 (as indicated by the downward facing arrow). Preferably, collection pad 20 is fabricated using an absorbent material, such as a sponge, thick cloth, foam, or an absorbent, antimicrobial material. Collection pad 20 may be disposable or reusable. Preferably, collection pad 20 is removable from sanitizing device 16.

Figure 12:
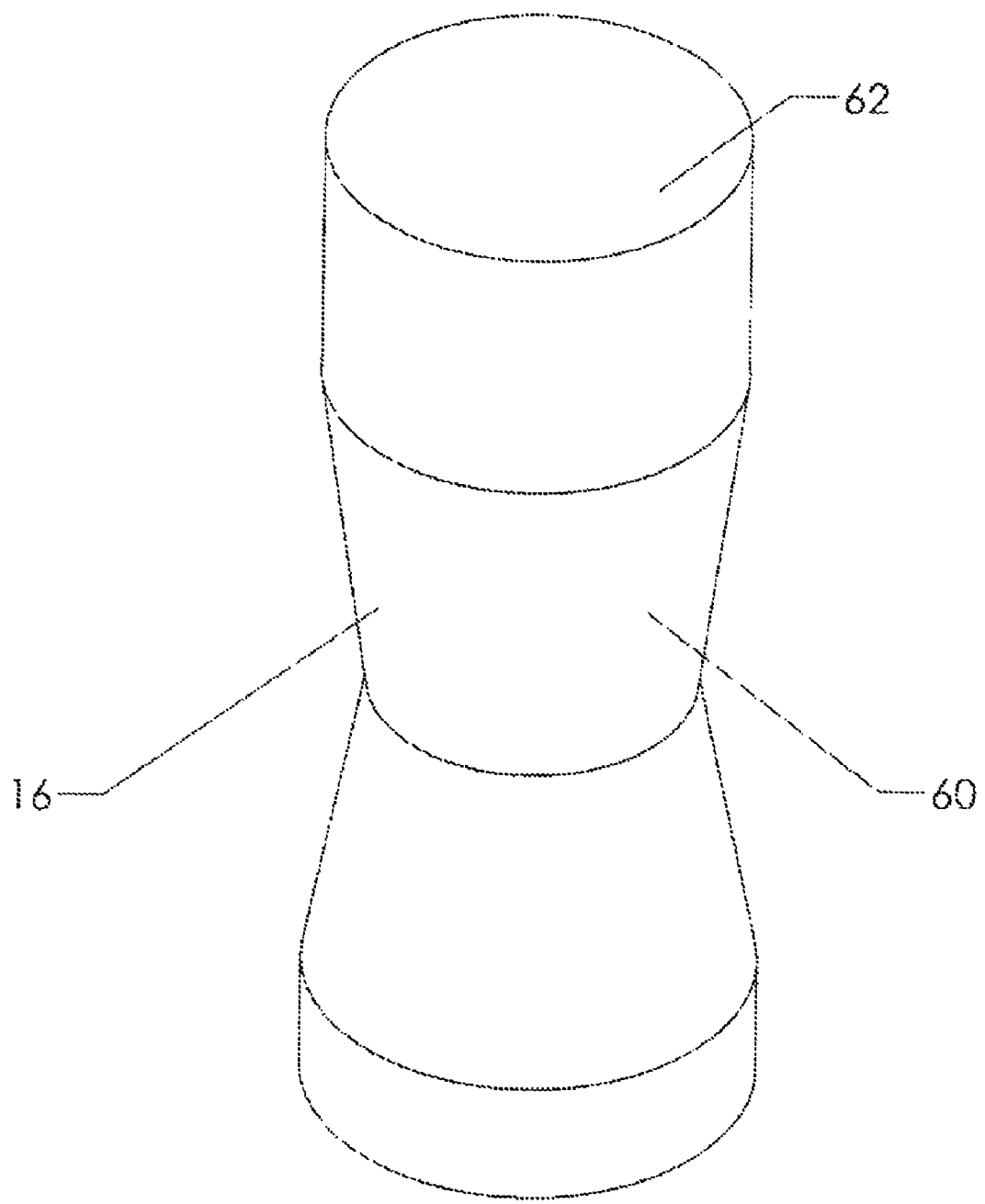
FIG. 12 is a perspective view, showing the embodiment of FIG. 10 with the device cover on the bulb receiver.

FIG. 12 shows an alternate embodiment of the present invention. This embodiment includes chamber lid 62. Chamber cover 62 preferably locks onto the main body 60 of sanitizing device 16. In the case where ultraviolet light bulb 82 produces ozone, device cover 62 insures ozone does not escape the chamber while in use. Instead, a high enough concentration of ozone is produced in order to sanitize the inner and outer surfaces of bulb syringe 10. A fan assembly (or another air circulation device) may be used in order to circulate the ozone within the sealed chamber. In the case where sanitization system 68 uses ionization, chamber lid 62 would allow for the accumulation of ions.

Figure 13:
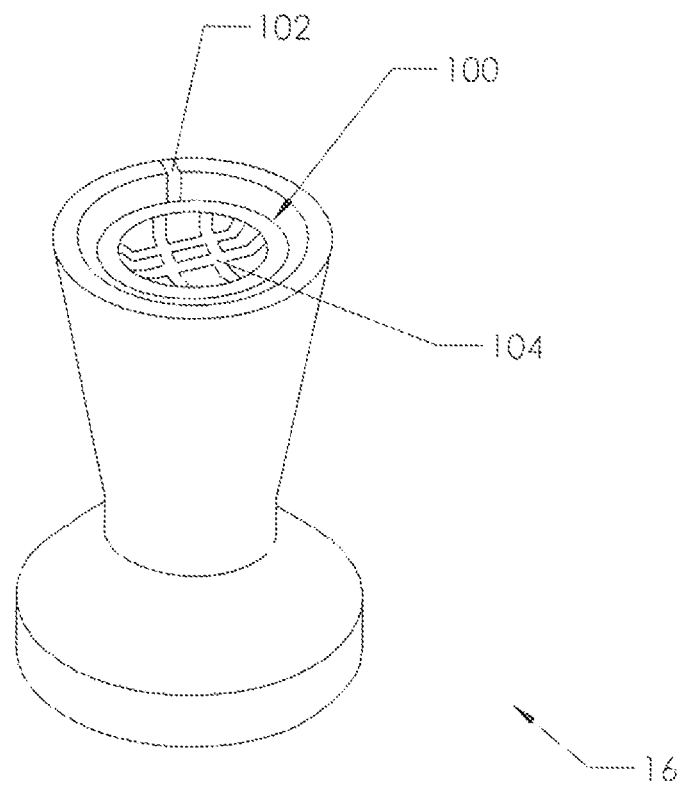
FIG. 13 is a perspective view, showing the embodiment of FIG. 10 with a retaining device attached to the receiver.
Figure 14:
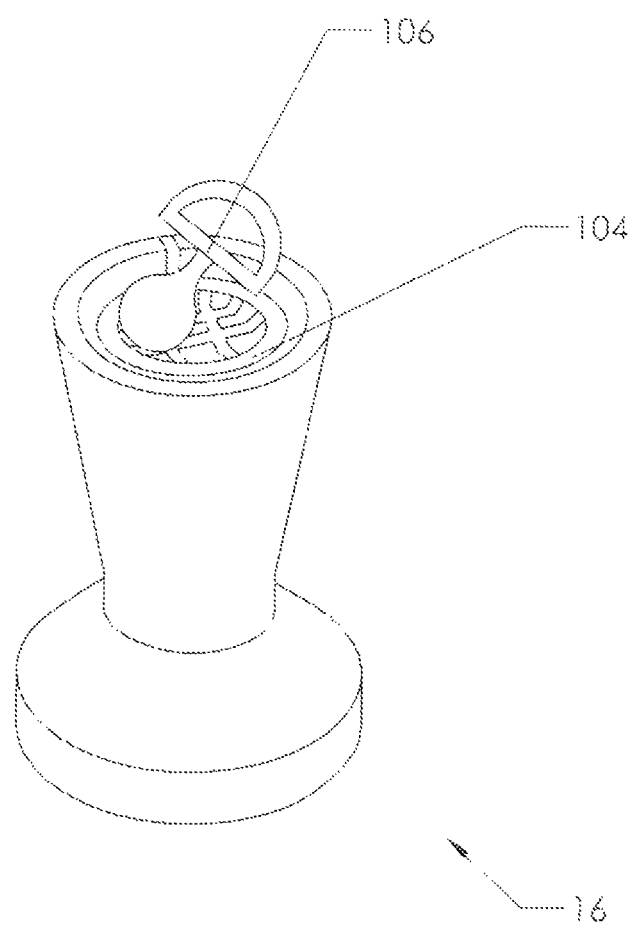
FIG. 14 is a perspective view, showing the embodiment of FIG. 10 with a retaining device attached to the receiver and containing a pacifier.

Another application of the embodiment shown in FIGS. 10-12 is shown in FIG. 13. Preferably, sanitizing device 16 includes retaining device 100. Preferably, retaining device 100 includes attachment hook 102 and basket 104. As illustrated, basket 104 is preferably woven. Preferably, hook 102 attaches to receiver 52. Once attached, the user can place items into basket 104 to be sanitized. One such example is shown in FIG. 14. Pacifier 106 is inserted into basket 104 in order to be sanitized by sanitizing device 16. Of course, many other small objects can be placed into basket 104 to be sanitized. A pacifier 106 is just one possible example of something that one is constantly cleaning and sanitizing. After pacifier 106 is placed in basket 104, chamber lid 62 can be placed over sanitizing device 16. This would allow ozone or ions to accumulate near the top portion where pacifier 106 is resting. Of course, whether there are ions or ozone depends on the sanitization system 68 and sanitization method—ozone production or ionization. The reader will note that when retaining device 100 is placed on receiver 52, beam 48 is not be broken, and the sanitization process does not start. In this case, a manual switch is used to activate the sanitization process.

Referring back to the embodiment shown in FIG. 2, the reader will note that pacifier 106 can easily rest in receiver 52. This would allow the user to place one or more pacifiers 106 into receiver 52 in order to sanitize multiple pacifiers 106 at once. In addition, retaining device 100 can be adapted to fit over receiver 52 on base 64. In one case retaining device 100 is raised, thereby positioning pacifier 106 closer to nozzle 84.

Those familiar with the art will know that many bulb syringes 10 are manufactured with different dimensions and proportions. The invention may easily accommodate different sizes by making the distance between base 16 and housing 66 adjustable. For example, in the embodiment of FIG. 2, the two housing 66 may be configured to slide adjustably along the two supports 70. However, typically each bulb syringe 10 has the same general shape—a small opening connected to a narrow conduit, and a large hollow bulb. The reader will note that the present invention is constructed such that multiple bulb syringes 10 can be sanitized using the device. In addition, those familiar with the art will know that there is one syringe 10 that is used by the majority of users. Of course, this syringe is issued by the hospital upon birth of a child.

In summary, the inventive system pumps a sanitizing gas into the open end of a bulb syringe in order to sanitize its interior. The sanitizing gas may be anything suitable for killing unwanted agents within the bulb. The examples described include a bi-polar ionization system for creating ionized air and a UV-based ozone production system for producing ozone-enriched air. Other sanitizing gas production systems may be used as well.

A fan has been described in the disclosed embodiments for pumping the sanitizing gas into the bulb syringe. One could also use a diaphragm pump or a centrifugal pump. Any device that produces positive flow can work, though obviously some devices will be more efficient than others.

The preceding description contains significant detail regarding the novel aspects of the present invention. It should not be construed, however, as limiting the scope of the invention but rather as providing illustrations of the preferred embodiments of the invention. Thus, the scope of the invention should be fixed by the following claims, rather than by any examples given.

Having described our invention, we claim:

1. A sanitizing device for sanitizing a bulb syringe having a spherical end and an open end including an opening, comprising:
   a. a bulb receiver configured to receive and hold said spherical end of said bulb syringe;
   b. a nozzle configured to engage said open end of said bulb syringe, said nozzle being separated from said bulb receiver and including a nozzle exit, configured so that said nozzle exit lies within said opening of said bulb syringe and said spherical end of said bulb syringe lies within said bulb receiver;
   c. a sanitizing gas production system configured to produce a sanitizing gas; and
   d. a gas pumping device configured to force said sanitizing gas through said nozzle exit in said nozzle, thereby flooding said bulb syringe with said sanitizing gas.

2. A sanitizing device as recited in claim 1, wherein said sanitizing gas is ionized air.

3. A sanitizing device as recited in claim 2, wherein said sanitizing gas production system comprises a bi-polar ionizer configured to produce positive ions and negative ions in air.

4. A sanitizing device as recited in claim 3, wherein said gas pumping device is a fan.

5. A sanitizing device as recited in claim 1, wherein said sanitizing gas is ozone-enriched air.

6. A sanitizing device as recited in claim 5, wherein said sanitizing gas production system comprises an ultraviolet light source configured to create said ozone-enriched air.

7. A sanitizing device as recited in claim 6, wherein said gas pumping device is a fan.

8. A sanitizing device as recited in claim 1, further comprising an array of openings around said nozzle, said array being configured to direct said sanitizing gas toward an exterior of said bulb syringe.

9. A sanitizing device as recited in claim 3, further comprising an array of openings around said nozzle, said array being configured to direct said sanitizing gas toward an exterior of said bulb syringe.

10. A sanitizing device as recited in claim 1, further comprising a removable cover.

11. A sanitizing device for sanitizing a bulb syringe having a spherical end and an open end including an opening, comprising:
    a. a bulb receiver including a tapered opening configured to receive and hold said bulb syringe;
    b. a nozzle configured to engage said open end of said bulb syringe as said bulb receiver holds said bulb syringe, said nozzle being separated from said bulb receiver and including a nozzle exit, configured so that said nozzle exit lies within said opening of said bulb syringe;
    c. a sanitizing gas production system configured to produce a sanitizing gas; and
    d. a gas pumping device configured to force said sanitizing gas through said nozzle exit in said nozzle, thereby flooding said bulb syringe with said sanitizing gas.

12. A sanitizing device as recited in claim 11, wherein said sanitizing gas is ionized air.

13. A sanitizing device as recited in claim 12, wherein said sanitizing gas production system comprises a bi-polar ionizer configured to produce positive ions and negative ions in air.

14. A sanitizing device as recited in claim 13, wherein said gas pumping device is a fan.

15. A sanitizing device as recited in claim 11, wherein said sanitizing gas is ozone-enriched air.

16. A sanitizing device as recited in claim 15, wherein said sanitizing gas production system comprises an ultraviolet light source configured to create said ozone-enriched air.

17. A sanitizing device as recited in claim 16, wherein said gas pumping device is a fan.

18. A sanitizing device as recited in claim 11, further comprising an array of openings around said nozzle, said array being configured to direct said sanitizing gas toward an exterior of said bulb syringe.

19. A sanitizing device as recited in claim 13, further comprising an array of openings around said nozzle, said array being configured to direct said sanitizing gas toward an exterior of said bulb syringe.

20. A sanitizing device as recited in claim 11, further comprising a removable cover.

* * * * *